(12) United States Patent
Park et al.

(10) Patent No.: US 11,077,170 B2
(45) Date of Patent: Aug. 3, 2021

(54) ANTIMICROBIAL PEPTIDE FROM SKATE SKIN AND USES THEREOF

(71) Applicant: INDUSTRY-ACADEMIC COOPERATION FOUNDATION, CHOSUN UNIVERSITY, Gwangju (KR)

(72) Inventors: Yoonkyung Park, Jeollanam-do (KR); Jong-Kook Lee, Jeollanam-do (KR)

(73) Assignee: INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 0 days.

(21) Appl. No.: 16/648,043

(22) PCT Filed: Sep. 7, 2018

(86) PCT No.: PCT/KR2018/010459
§ 371 (c)(1),
(2) Date: Mar. 17, 2020

(87) PCT Pub. No.: WO2019/059572
PCT Pub. Date: Mar. 28, 2019

(65) Prior Publication Data
US 2020/0254057 A1 Aug. 13, 2020

(30) Foreign Application Priority Data
Sep. 22, 2017 (KR) .................. 10-2017-0122499

(51) Int. Cl.
*A61K 38/10* (2006.01)
*A61K 31/43* (2006.01)
*A61K 8/64* (2006.01)
*A01N 33/08* (2006.01)
*A01N 37/46* (2006.01)
*A61Q 19/00* (2006.01)
*C07K 7/08* (2006.01)
*A61K 38/17* (2006.01)
*A23K 20/147* (2016.01)
*A23K 20/195* (2016.01)
*A23L 3/3463* (2006.01)

(52) U.S. Cl.
CPC .......... *A61K 38/1706* (2013.01); *A01N 33/08* (2013.01); *A23K 20/147* (2016.05); *A23K 20/195* (2016.05); *A23L 3/34635* (2013.01); *A61K 8/64* (2013.01); *A61Q 19/00* (2013.01)

(58) Field of Classification Search
CPC .. A61K 2300/00; A61K 38/10; A61K 31/165; A61K 31/43; A61K 31/7036; A61K 38/1706; A61K 8/64; A01N 33/08; A01N 37/46; A61Q 19/00; C07K 7/08
See application file for complete search history.

(56) References Cited

U.S. PATENT DOCUMENTS

2007/0083334 A1* 4/2007 Mintz ................. A61P 29/00
702/19

FOREIGN PATENT DOCUMENTS

| KR | 10-2012-0134501 A | 12/2012 |
|---|---|---|
| KR | 10-2013-0104718 A | 9/2013 |
| KR | 10-2016-0055343 A | 5/2016 |
| KR | 10-2017-0032689 A | 3/2017 |
| KR | 10-1734331 B1 | 5/2017 |

OTHER PUBLICATIONS

International Search Report for PCT/KR2018/010459 dated Apr. 22, 2019.
Thomas E. Creighton, "Proteins; structures and molecular principles.", W. H. Freeman and Company New York, p. 286-295, 1983.
Ana Segura et al., "Snakin-1, a Peptide from Potato That Is Active Against Plant Pathogens" Mol Plant Microbe Interact., vol. 12, No. 1, p. 16-23, 1999.
NCBI Genbank Accession No. KFE45468.1, "20G-Fe(II) Oxygenase [Pseudomonas syringae]", 2014.

* cited by examiner

Primary Examiner — Julie Ha
(74) Attorney, Agent, or Firm — The PL Law Group, PLLC (57) ABSTRACT

A method for treating a microorganism or inflammation caused by the microorganism includes administering or applying a composition comprising an antimicrobial peptide with the amino acid sequence of SEQ ID NO: 1 to a subject in need thereof. Because the antimicrobial peptide with the amino acid sequence of SEQ ID NO: 1 exhibits an excellent antimicrobial activity against Gram-negative bacteria and Gram-positive bacteria and also low cytotoxicity for human erythrocytes, it can be advantageously used for various applications.

19 Claims, 6 Drawing Sheets
Specification includes a Sequence Listing.

ANTIMICROBIAL PEPTIDE FROM SKATE SKIN AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/010459 filed on Sep. 7, 2018, which claims priority to the benefit of Korean Patent Application No. 10-2017-0122499 filed in the Korean Intellectual Property Office on Sep. 22, 2017, the entire contents of which are incorporated herein by reference.

TECHNICAL FIELD

The present invention relates to a novel antimicrobial peptide derived from skate skin and uses thereof.

BACKGROUND ART

All living organisms are known to naturally produce peptides having antibiotic activity, and it is also reported that this antibiotic activity of peptides plays a key role in host defense and innate immune system. Depending on the amino acid sequence, those peptides having antibiotic activity are classified into a (3-sheet peptide rich in cysteine, an α-helical amphipathic molecule, a proline-rich peptide, or the like. Furthermore, other than the peptides produced inside a living organism, bacteriocin secreted for competing with other homo bacteria or hetero bacteria present in the neighborhood is also well known as an antibiotic material for removing harmful bacteria. Bacteriocin is classified into three different types, i.e., lantibiotics, nonlantibiotics, and signal peptide, depending on the structure. With an antibiotic peptide or bacteriocin which is produced in a living organism to exhibit the antibiotic activity, problems like tolerance to antibiotics, shock caused by antibiotics, or the like can be solved.

Accordingly, various studies are being made to develop natural antibiotics which can replace conventional antibiotics. The natural antibiotics mean an antimicrobial agent with no toxicity or minimal toxicity for human body that is obtained by maximizing a biochemical or physiological difference from a plant or a microorganism and inhibiting/ controlling selectively the growth of viruses, bacteria, yeast, fungi, or the like.

As one of the natural antimicrobial agents which have been reported until now, propolis is a natural anti-oxidant, and, with extraction of resin components from a tree containing flavonoids and mixing them with saliva and enzyme, protective materials for protecting honey, queen bee, or the like are applied inside a beehive. Various vitamins, amino acids, flavonoids or the like that are contained in propolis, which is effective for protection by a worker bee against bacterial infection, play a role of promoting cell metabolism, and terpens or the like exhibits an anticancer and antibacterial effect and suppresses prostaglandins which cause inflammation and pains in a living body, and thus yielding strengthened immune system. However, as pollens are also included in propolis, pollen allergy may occur and pregnant women are encouraged to consult a physician first before taking propolis.

As one of the Korean traditional home remedies, fermented skate as strong alkaline food is known to be effective for treating osteoporosis and skin conditions including age spots, freckles, or the like, and fermented skate soup is known to be highly effective for suppressing stomach flu and hangover, prophylaxis of stroke, renal failure, or the like. It is also known that skate plays a role of natural antimicrobial agent.

Meanwhile, in Korean Patent Registration No. 1263452, "Novel antibiotic peptide isolated from *Atrina pectinata* and use thereof" is disclosed, and, in Korean Patent Registration No. 1734331, "Novel antibiotic peptide isolated from Korean sea cucumber and use thereof" is disclosed. However, no descriptions are included in those documents regarding the novel antimicrobial peptide derived from skate skin and uses thereof of the present invention.

SUMMARY

The present invention is devised under the circumstances described above, and, by extracting, isolating, and purifying a fraction with antibacterial activity from skate (*Okamejei kenojei*) skin as a natural biological material, and determining a novel peptide exhibiting an excellent antimicrobial activity against Gram-positive bacteria and Gram-negative bacteria, and low cytotoxicity for human erythrocytes, the inventors of the present invention completed the present invention.

In order to solve the problems described above, the present invention provides an antimicrobial peptide consisting of the amino acid sequence of SEQ ID NO: 1 which is derived from skate (*Okamejei kenojei*) skin.

The present invention further provides antibiotics comprising the aforementioned antimicrobial peptide as an effective component.

The present invention further provides an antibiotic quasi-drug composition comprising the aforementioned antimicrobial peptide as an effective component.

The present invention further provides a method for antimicrobial treatment in a subject including administering a pharmaceutically effective amount of the aforementioned antimicrobial peptide to a subject.

The present invention further provides an antibiotic cosmetic composition comprising the aforementioned antimicrobial peptide as an effective component.

The present invention further provides an antibiotic food additive comprising the aforementioned antimicrobial peptide as an effective component.

The present invention further provides an antibiotic animal feed additive comprising the aforementioned antimicrobial peptide as an effective component.

The present invention further provides antibiotic biopesticides comprising the aforementioned antimicrobial peptide as an effective component.

The present invention still further provides a preservative composition comprising the aforementioned antimicrobial peptide as an effective component.

Because the novel antimicrobial peptide of the present invention exhibits not only an excellent antimicrobial activity but also low cytotoxicity for human cells, it can be advantageously used as an effective component of antibiotics, a cosmetic composition, a food additive, an animal feed additive, biopesticides, or the like. Furthermore, since the skate skin from which the peptide of the present invention is derived is a waste material that is hardly used, it is advantageous in terms of easy availability of raw materials and low cost, and thus the antimicrobial peptide of the present invention is expected to be advantageously used as a natural antimicrobial agent.

DETAILED DESCRIPTION

To achieve the purpose of the present invention, the present invention provides an antimicrobial peptide consisting of the amino acid sequence of SEQ ID NO: 1 which is derived from skate (*Okatmejei kenojei*) skin.

The novel antimicrobial peptide having the amino acid sequence of SEQ ID NO: 1 is isolated from skin of a skate, and may have low cytotoxicity for human-derived cells, but it is not limited thereto. The antimicrobial peptide can be extracted and isolated from skate skin by a method for extracting proteins/peptides that is well known in the pertinent art. It can be also produced by a method for synthesis of peptide that is well known in the pertinent art. As for the method for synthesis, synthesis is preferably carried out according to a method for chemical synthesis (W. H. Freeman and Co., Proteins; structures and molecular principles, 1983). More preferably, synthesis is carried out by a solution phase peptide synthesis, a solid-phase peptide synthesis, a fragment condensation method, but it is not limited thereto.

It is preferable that the antimicrobial peptide has an antimicrobial activity against Gram-negative bacteria or Gram-positive bacteria, but it is not limited thereto.

Gram-negative bacteria are every Gram-negative bacteria that are known in the pertinent art including Gram-negative bacteria of *Escherichia* sp., *Pseudomonas* sp., *Acinetobacter* sp., *Salmonella* sp., *Leptospira* sp., and *Rickettsia* sp. Gram-negative bacteria are preferably the Gram-negative bacteria of *Escherichia* sp., *Pseudomonas* sp., or *Acinetobacter* sp. Gram-negative bacteria are most preferably at least one selected from the group consisting of *Escherichia coli, Pseudomonas aeruginosa*, and *Acinetobacter baumannii*, but they are not limited thereto.

Gram-positive bacteria are every Gram-positive bacteria that are known in the pertinent art including Gram-positive bacteria of *Staphylococcus* sp., *Listeria* sp., *Lactobacillus* sp., and *Bacillus* sp. Gram-positive bacteria are preferably Gram-positive bacteria of *Staphylococcus* sp. Gram-positive bacteria are most preferably *Staphylococcus aureus*, but they are not limited thereto.

Other than the above Gram-negative bacteria and Gram-positive bacteria, the antimicrobial peptide of the present invention may have an antimicrobial activity against bacteria having tolerance to antibiotics. The bacteria having tolerance to antibiotics may be at least one selected from the group consisting of *Escherichia coli, Pseudomonas aeruginosa, Staphylococcus aureus*, and *Acinetobacter baumannii* having tolerance to antibiotics, but they are not limited thereto.

Examples of the antibiotics include, although not limited thereto, aminoglycoside-based (aminoglycoside, gentamycin, neomycin, and the like), penicillin-based (ampicillin and the like), sulfonamide-based, beta-lactam based (beta-lactam, amoxicillin/clavulanic acid, and the like), chloramphenicol-based, erythromycin-based, florfenicol-based, fosfmycin-based, kanamycin-based, lincomycin-based, meticillin-based, quinolone-based, streptomycin-based, tetracycline-based, trimethoprim-based, and vancomycin-based antibiotics.

The present invention further provides antibiotics comprising the aforementioned antimicrobial peptide as an effective component.

The antimicrobial peptide of the present invention is a peptide having the amino acid sequence of SEQ ID NO: 1, as described in the above. The antimicrobial peptide of the present invention which is derived from skate skin exhibits a strong antimicrobial activity against Gram-positive bacteria, Gram-negative bacteria, and bacteria having tolerance to antibiotics and also has low cytotoxicity for human-derived cells, and thus it can be advantageously used as an effective component of antimicrobial antibiotics.

For clinical administration, the peptide of the present invention can be administered parenterally, and it can be used in the form of a common pharmaceutical preparation. Parenteral administration may mean administration via a route other than oral administration like rectal, intravenous, intraperitoneal, intramuscular, intraarterial, transdermal, nasal, inhalational, intraocular, and subcutaneous administration. When the antimicrobial peptide of the present invention is used as a pharmaceutical, one or more effective components exhibiting the same or similar activity may be additionally included.

Namely, the antimicrobial peptide of the present invention can be indeed administered as various parenteral preparations, and, in case of having a preparation, production is made by using a diluent or a vehicle such as filler, bulking agent, binding agent, moisturizing agent, disintegrating agent, or surfactant that are commonly used for producing a preparation. In a preparation for parenteral administration, a sterilized aqueous solution, a non-soluble preparation, a suspension, an oil preparation, a freeze-dried preparation, and a suppository are included. As a water insoluble solvent or a suspending solvent, propylene glycol, polyethylene glycol, or vegetable oil such as olive oil, and injectable ester such as ethylolate can be used. As a base for a suppository, witepsol, macrogol, tween 61, cacao fat, laurin fat, glycerogelatin, or the like can be used.

Furthermore, the antimicrobial peptide of the present invention can be used after being admixed with various pharmaceutically acceptable carriers such as physiological saline or organic solvent. To enhance the stability or absorption property, carbohydrates such as glucose, sucrose, or dextran, anti-oxidants such as ascorbic acid or glutathione, chelating agents, low molecular weight proteins, or other stabilizers can be used as a pharmaceutical agent.

Effective dose of the antimicrobial peptide of the present invention is 0.1 to 2 mg/kg, and preferably 0.5 to 1 mg/kg. Administration can be made 1 to 3 times a day.

Total effective amount of the novel peptide of the present invention in the antibiotics of the present invention can be administered to a patient as a single dose in bolus form or infusion during a relatively short period of time, and it can be also administered according to a fractionated treatment protocol by which multiple dose is administered for a long period of time. With regard to the concentration described above, the effective dose is determined by considering not only the pharmaceutical administration route and number of treatment but also other various factors including age, health state, or the like of a patient. Thus, by considering them, a person having common knowledge in the pertinent art may determine suitable effective dose depending on specific use of the novel peptide of the present invention as antibiotics.

The present invention further provides an antibiotic quasi-drug composition comprising the aforementioned antimicrobial peptide as an effective component When the composition of the present invention is used as a quasi-drug additive, the antimicrobial peptide may be directly added or used with other quasi-drug or quasi-drug components, and it can be suitably used according to a general method. Blending amount of the effective component can be suitably determined depending on the purpose of use.

The quasi-drug composition of the present invention is preferably a sterilizing cleanser, a shower foam, a mouth wash, a water tissue, a liquid soap, a hand wash, a humidifier filler, a mask, an ointment, a patch, or a filter filler, although it is not limited thereto.

The present invention further provides a method for antimicrobial treatment in a subject including administering a pharmaceutically effective amount of the aforementioned antimicrobial peptide to a subject. The subject may be a mammal excluding human, but it is not limited thereto.

The present invention further provides an antibiotic cosmetic composition comprising the aforementioned antimicrobial peptide as an effective component.

In the cosmetic composition of the present invention, components commonly used for a cosmetic composition are included in addition to the antimicrobial peptide, and examples thereof include a common auxiliary agent such as an anti-oxidant, a stabilizing agent, a solubilizing agent, vitamin, a pigment, or a fragrance, and a carrier.

In the cosmetic composition of the present invention, the peptide of the present invention may be added in an amount of 0.1 to 50% by weight, and preferably 1 to 10% by weight to the cosmetic composition.

The cosmetic composition of the present invention may be produced in any formulation that is produced commonly in the pertinent art. For example, it can be produced as a formulation such as a solution, a suspension, an emulsion, paste, gel, cream, lotion, powder, a soap, a surfactant-containing cleanser, oil, powder foundation, emulsion foundation, wax foundation, or spray, but it is not limited thereto. More specifically, it can be produced as a formulation such as softening cosmetic water (skin water), nutritive cosmetic water (milk lotion), nutritive cream, massage cream, essence, eye cream, cleansing cream, cleansing foam, cleansing water, pack, spray, or powder.

When the formulation of the present invention is paste, cream, or gel, animal oil, vegetable oil, wax, paraffin, starch, tragacanth, cellulose derivatives, polyethylene glycol, silicone, bentonite, silica, talc, or zinc oxide can be used as a carrier component.

When the formulation of the present invention is powder or spray, lactose, talc, silica, aluminum hydroxide, calcium silicate, or polyamide powder can be used as a carrier component. When the formulation is spray, in particular, a propellant such as chlorofluorohydrocarbon, propane/butane, or dimethyl ether may be additionally included.

When the formulation of the present invention is a solution or an emulsion, a solvent, a solubilizing agent, or an emulsifying agent is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

When the formulation of the present invention is a suspension, a liquid diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, or tragacanth can be used as a carrier component.

When the formulation of the present invention is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamine, vegetable oil, lanolin derivatives, or ethoxylated glycerol fatty acid ester can be used as a carrier component.

The present invention further provides an antibiotic food additive comprising the aforementioned antimicrobial peptide as an effective component.

When the peptide of the present invention is used as a food additive, the peptide may be directly added or used with other food components, and it can be suitably used according to a general method. Blending amount of the effective component can be suitably determined depending on the purpose of use. In general, the peptide of the present invention is added in an amount of 15 parts by weight or less, and preferably 10 parts by weight or less relative to peptide raw materials. However, in case of application for a long period of time, the blending amount may be lower than the aforementioned range. As there is no problem in terms of the stability, the effective component may be used in an amount that is higher than the aforementioned range.

Type of the food is not particularly limited. Examples of the food to which the additive can be added include meat, sausage, bread, chocolate, candies, snacks, biscuits, pizza, ramen, other noodles, gums, dairy products including ice cream, various kinds of soup, beverage, tea, drink, alcohol beverage, and vitamin complex, and all foods in general sense are included therein.

The present invention further provides an antibiotic animal feed additive comprising the aforementioned antimicrobial peptide as an effective component.

The animal feed composition of the present invention has an effect of replacing existing antibiotics, inhibiting the growth of harmful pathogenic food bacteria to improve the health state of an animal, enhancing the body weight and meat quality of livestock, and enhancing the milk production amount and immunity of livestock. The animal feed composition of the present invention can be produced in the form of fermented animal feed, complete animal feed, pellets, silage, or the like.

The fermented animal feed can be produced by adding various microbes or enzymes other than the peptide of the present invention to ferment organic matters, and the complete animal feed can be produced by admixing the peptide of the present invention with various kinds of common animal feed. Animal feed in pellet form can be produced by applying heat and pressure to a complete feed in a pelletizing machine, and silage can be produced by fermenting forage with the microbes of the present invention. Fermented wet animal feed can be produced by, after collecting and transporting organic matters and admixing them with a vehicle at a certain ratio for moisture control and sterilization, fermenting organic matters like food waste at a temperature suitable for fermentation for 24 hours or longer to adjust moisture content to about 70%. Fermented dry animal feed can be produced according to adjustment of the moisture content to 30% to 40% or so by providing fermented wet animal feed additionally to a drying process.

The present invention further provides antibiotic biopesticides comprising the aforementioned antimicrobial peptide as an effective component.

The present invention still further provides a preservative composition comprising the aforementioned antimicrobial peptide as an effective component.

The antimicrobial peptide of the present invention is a peptide having the amino acid sequence of SEQ ID NO: 1. The antimicrobial peptide of the present invention exhibits a strong antimicrobial activity against Gram-positive bacteria, Gram-negative bacteria, and bacteria having tolerance to antibiotics and also has low cytotoxicity for human-derived cells. Therefore, the antimicrobial peptide of the present invention can be advantageously used as an effective component of antibiotic biopesticides or a preservative composition.

Examples of the preservative composition include a cosmetics preservative and a pharmaceutical preservative. The preservative agent for food, cosmetics preservative, and pharmaceutical preservative are an additive which is used to prevent deterioration, degradation, discoloration, and chemical change of those products, and examples thereof include a sterilizer and an anti-oxidant. Also included are functional antibiotics having an activity of inhibiting growth or sterilizing degrading bacteria in food product and pharmaceutical product according to suppression of proliferation of microbes like bacteria, fungi, and yeast. As an ideal condition required for such preservative composition, the composition should not have any toxicity and should exhibit the effect even with a trace amount.

Hereinbelow, the present invention is explained in greater detail in view of the Examples. However, it is evident that the following Examples are given only for exemplification of the present invention and by no means the present invention is limited to the following Examples.

EXAMPLES

Example 1: Extraction of Protein from Skate Skin

By using a mortar and pestle, skate (*Okamejei kenojei*) skin added with liquid nitrogen was ground to powder, which was then mixed well with 50% methanol for 3 hours at 4° C. followed by centrifuge for 20 minutes at 12,000 rpm to extract proteins. As for the method of extracting proteins in the present invention, a well known method was employed with modification (Ana Segura et al. (1999) Mol Plant Microbe Interact., 12(1):16-23). After that, the extract was centrifuged for 30 minutes at 6,000×g, and only the supernatant was collected and purified by dialysis against deionized water using Spectra/Por 7: 3,500D MWCO) membrane (Spectrum Laboratories, Inc., USA) at 4° C.

Example 2. Measurement of Antimicrobial Activity

To measure the antimicrobial activity of the small-sized protein/peptide isolated from skate skin, which has been extracted in Example 1, the experiment was carried out as follows.

Specifically, *Escherichia coli* (CCARM 1229), *Pseudomonas aeruginosa* (KCTC 1637), *Acinetobacter baumannii* (KCTC 2508) or *Staphylococcus aureus* (CCARM 259237) were diluted such that they are present in $1 \times 10^5$ cells per well of a 96-well microtiter plate, and 100 µl of the medium (LB, NB+0.5% NaCl, NB, TSB) containing each strain were inoculated to a plate. As a negative control group, inoculation was made with each strain only, and, for the remaining plates, each strain was inoculated together with 100 µg of the sample purified in Example 1, and then they were incubated for 4 hours in an incubator at 37° C. After that, to visualize the antimicrobial activity, the plate inoculated only with each strain and the plate inoculated with each strain and the sample were examined under a microscope. As a result, it was observed that, compared to the plate inoculated only with each strain, cell growth with abnormal shape is yielded in the plate inoculated with each strain and the sample (FIG. 2).

Figure 1:
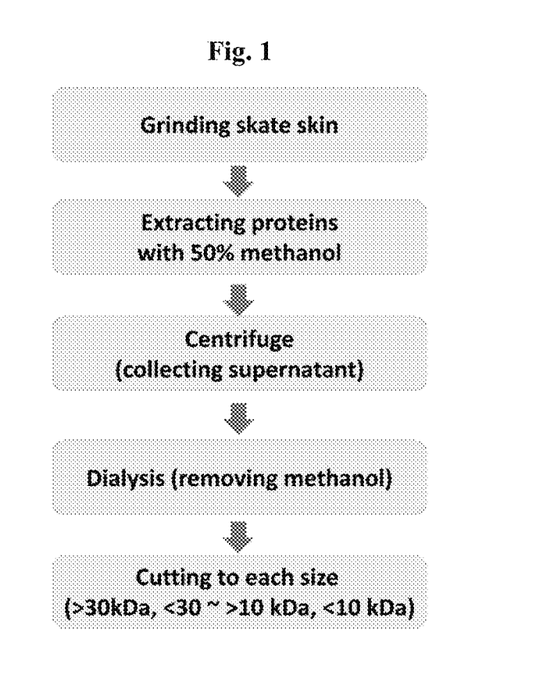
FIG. 1 is a schematic diagram showing the process of isolating the peptide of the present invention from skate (*Okamejei kenojei*) skin.
Figure 2:
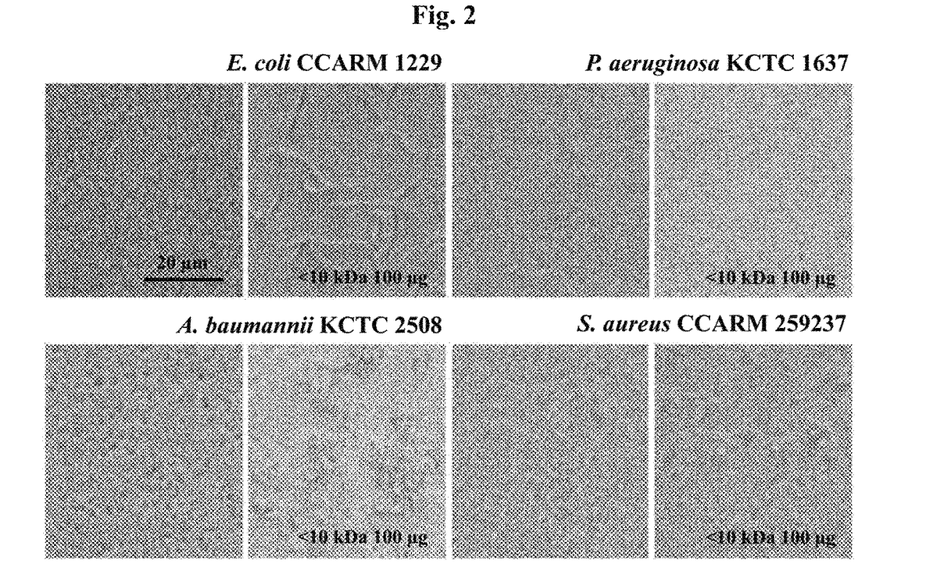
FIG. 2 shows the result of determining the antimicrobial activity for bacteria by using an extract (<10 kDa) extracted from skate skin, in which, for each bacteria, the left column shows the result obtained with no treatment with the extract and the right column shows the result obtained with a treatment with 100 μg extract.

FIG. 2 shows the result of determining the antimicrobial activity by using a sample of 10 kDa or less which has been extracted from skate skin. As a result of observing the growth level of bacterial cells for both the negative control group and test group, it was found that the sample of 10 kDa or less extracted from skate skin exhibits a strong antimicrobial activity.

Example 3. Reverse Phase HPLC and Measurement of Antimicrobial Activity

Figure 3A:
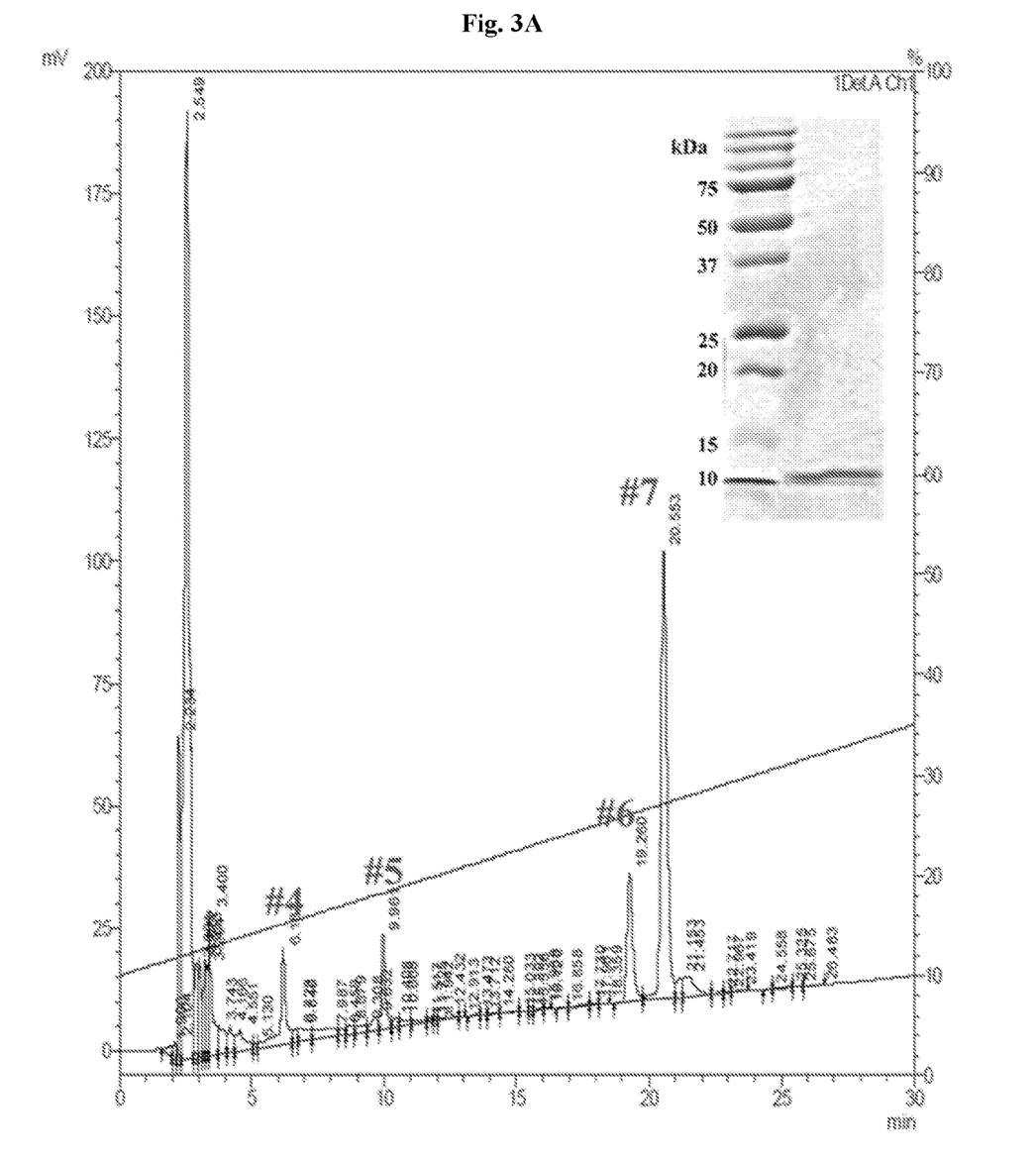
FIG. 3A shows the reverse phase high-performance liquid chromatography (RP-HPLC) results of the extract extracted from skate skin.

The <10 kDa sample of Example 1, which has been obtained from skate skin, was subjected to reverse phase high-performance liquid chromatography (reverse phase HPLC) using C18 column (4.6×250 mM; 4.6±0.3 µm particle; 12.0±1.0 nm pore; Shimadzu, Japan) to separate each peak. (See FIG. 3A) Specifically, after the elution based on linear gradient (10 to 65%, 2%/min, 30 min) of a buffer (acetonitrile B containing 0.5% TFA), the peak fractions were collected and the antimicrobial activity was measured.

Figure 3B:
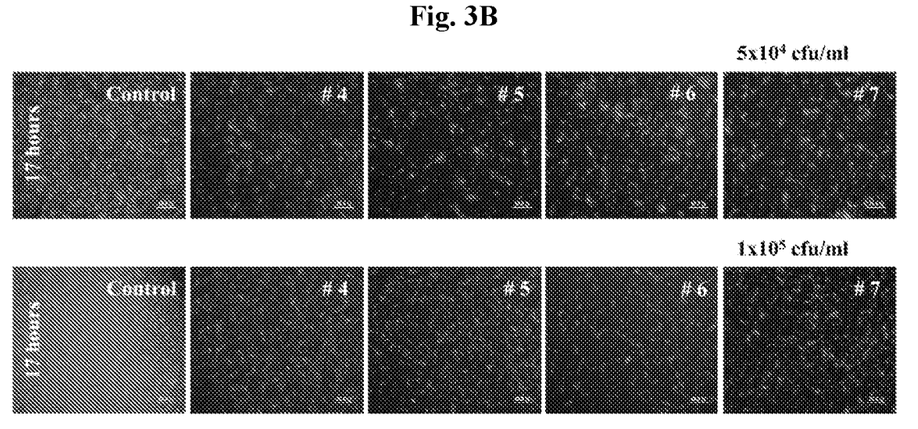
FIG. 3B shows the result of determining the antimicrobial activity for GFP+ *E. coli* after collecting the fractions of each peak by using RP-HPLC, wherein the fractions contain proteins of 10 kDa or less.

For the measurement of the antimicrobial activity, expression of GFP (green fluorescence protein) in *E. coli* was induced and examined. As for the number of *E. coli*, dilution was made so as to have $5 \times 10^4$ or $1 \times 10^5$ cells per well of a 96-well microtiter plate, and 10042 of the LB medium containing *E. coli* were inoculated to the plate. As a negative control group, *E. coli* was inoculated only, and, for the remaining plates, *E. coli* was inoculated together with each peak fraction obtained from the above reverse phase HPLC, and they were incubated for 4 hours in an incubator at 37° C. After that, to visualize the antimicrobial activity, the plate inoculated only with *E. coli* and the plate inoculated with *E. coli* and each elution fraction were examined under a microscope. As a result, a strong antimicrobial activity was shown from Peak Nos. 4, 5, 6 and 7 compared to the case inoculated with *E. coli* only, and it was found that the strong antimicrobial activity is maintained even when the cell number increases (FIG. 3B). In particular, a large amount was obtained by reverse phase HPLC from Peak No. 7, and, as a result of comparing it with the antimicrobial activity of other peaks, it was found to have a strong antimicrobial activity.

Example 4. HPLC Determination and Tricine SDS-PAGE

Figure 4:
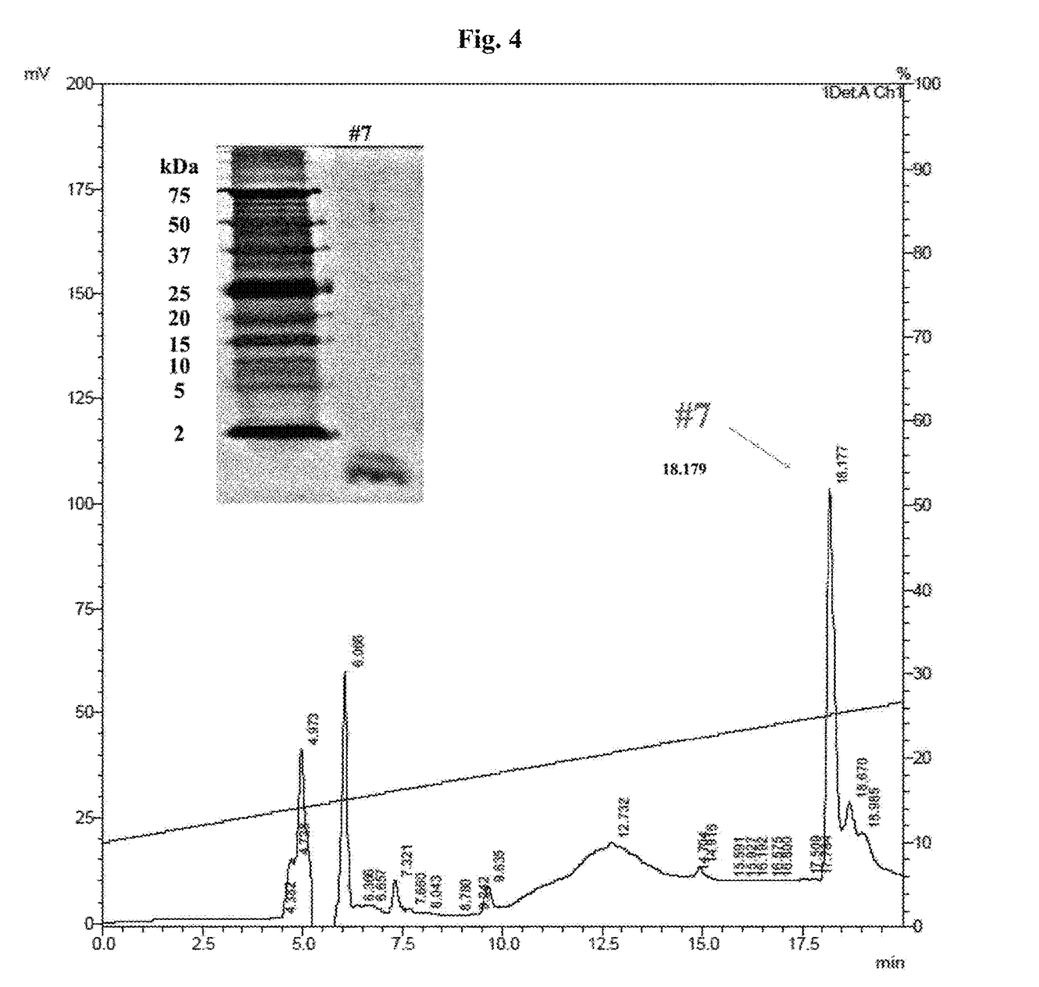
FIG. 4 shows the histogram for determining a peak of the peptide derived from skate skin by using LC-HPLC, and also the result of tricine SDS-PAGE electrophoresis.

Peak No. 7 sample obtained from Example 3 was purified by subjecting it to reverse phase HPLC using C18 column (4.6×250 mM; 4.6±0.3 μm particle; 12.0±1.0 nm pore; Shimadzu, Japan). Specifically, after the elution based on linear gradient (10 to 65%, 2%/min, 30 min) of a buffer (acetonitrile B containing 0.5% TFA), each peak fraction was subjected to tricine SDS-PAGE to determine the molecular weight. The gel obtained after electrophoresis was stained by silver staining to determine the molecular weight. As a result, it was found that, based on the estimation made in view of the size markers, Peak No. 7 sample with strong antimicrobial activity is a protein/peptide with very small size which is present at 2 kDa or less (FIG. 4).

Example 5. Determination of Molecular Weight and Amino Acid Sequence

The peptide purified from Example 4 was dissolved in 6 N hydrochloric acid, hydrolyzed for 22 hours at 110° C., and dried. Thereafter, the amino acid sequence was determined by using an amino acid analyzer. Furthermore, by using a mass analyzer (Kratos, AXIMA-CFR; Shimadzu), molecular weight of that peptide with known sequence was measured.

melittin as a known antimicrobial peptide was treated at the same concentrations. By setting the absorbance of a treatment with 0.1% Triton X-100 at 100% as a control group that is served as a reference of hemolysis level of erythrocytes, the hemolysis rate of each peptide, i.e., hemolysis, was calculated using the following mathematical formula 1.

$$\text{Erythrocyte disrupting ability (\%)} = (\text{Absorbance } A - \text{Absorbance } B)/(\text{Absorbance } C - \text{Absorbance } B) \times 100 \quad [\text{Mathematical formula 1}]$$

(in the above formula, Absorbance A indicates the absorbance of a reaction solution treated with each peptide, in which the absorbance is measured at a wavelength of 414 nm; Absorbance B indicates the absorbance of a reaction solution treated with PBS, in which the absorbance is measured at a wavelength of 414 nm; and Absorbance C indicates the absorbance of a reaction solution treated with 1% Triton X-100, in which the absorbance is measured at a wavelength of 414 nm).

Figure 6:
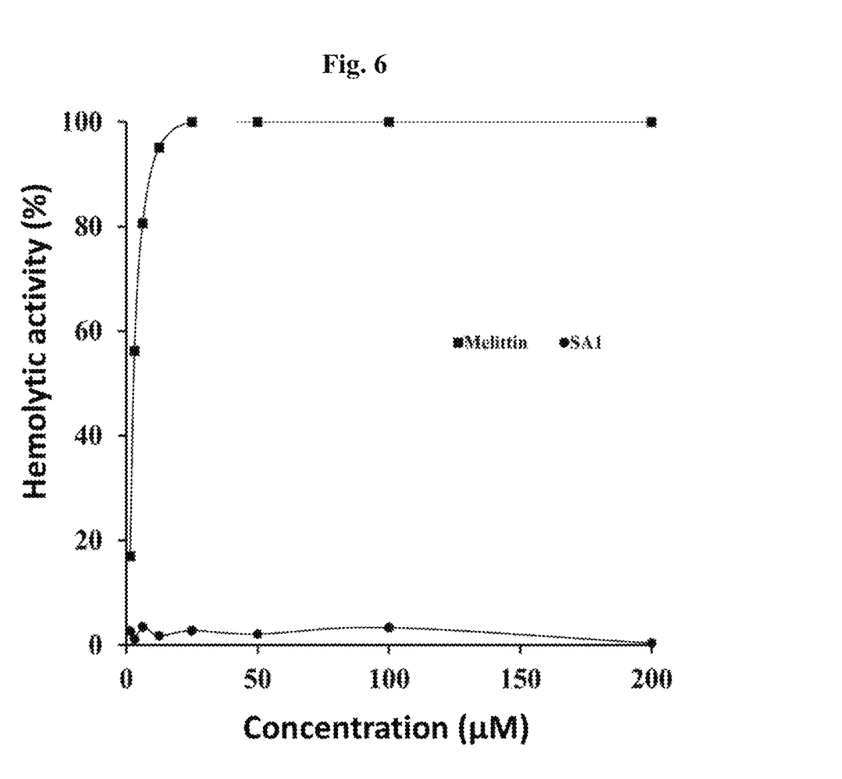
FIG. 6 shows the result of determining the hemolytic activity of the peptide derived from skate skin for human erythrocytes, in which SA1: antimicrobial peptide derived from skate skin, and Melittin: antimicrobial peptide derived from bee venom.

As a result, it was found that the skate skin-derived antimicrobial peptide (SA1) of the present invention shows a low hemolytic activity for human erythrocytes, thus indicating low cytotoxicity. On the other hand, melittin as an antimicrobial peptide derived from bee venom showed a high hemolytic activity of at least 55% at a low concentration like 3.125 μM, indicating that it is a peptide with high cytotoxicity (FIG. 6).

A sequence listing electronically submitted with the present application on Mar. 17, 2020 as an ASCII text file named 20200317_Q27520GR02_TU_SEQ, created on Mar. 12, 2020 and having a size of 1000 bytes, is incorporated herein by reference in its entirety.

```
                       SEQUENCE LISTING

<160> NUMBER OF SEQ ID NOS: 1

<210> SEQ ID NO 1
<211> LENGTH: 13
<212> TYPE: PRT
<213> ORGANISM: Okamejei kenojei

<400> SEQUENCE: 1

Tyr Glu Pro Gly Gln Val Arg Cys Cys Leu Met Pro Ala
1               5                   10
```

Figure 5:
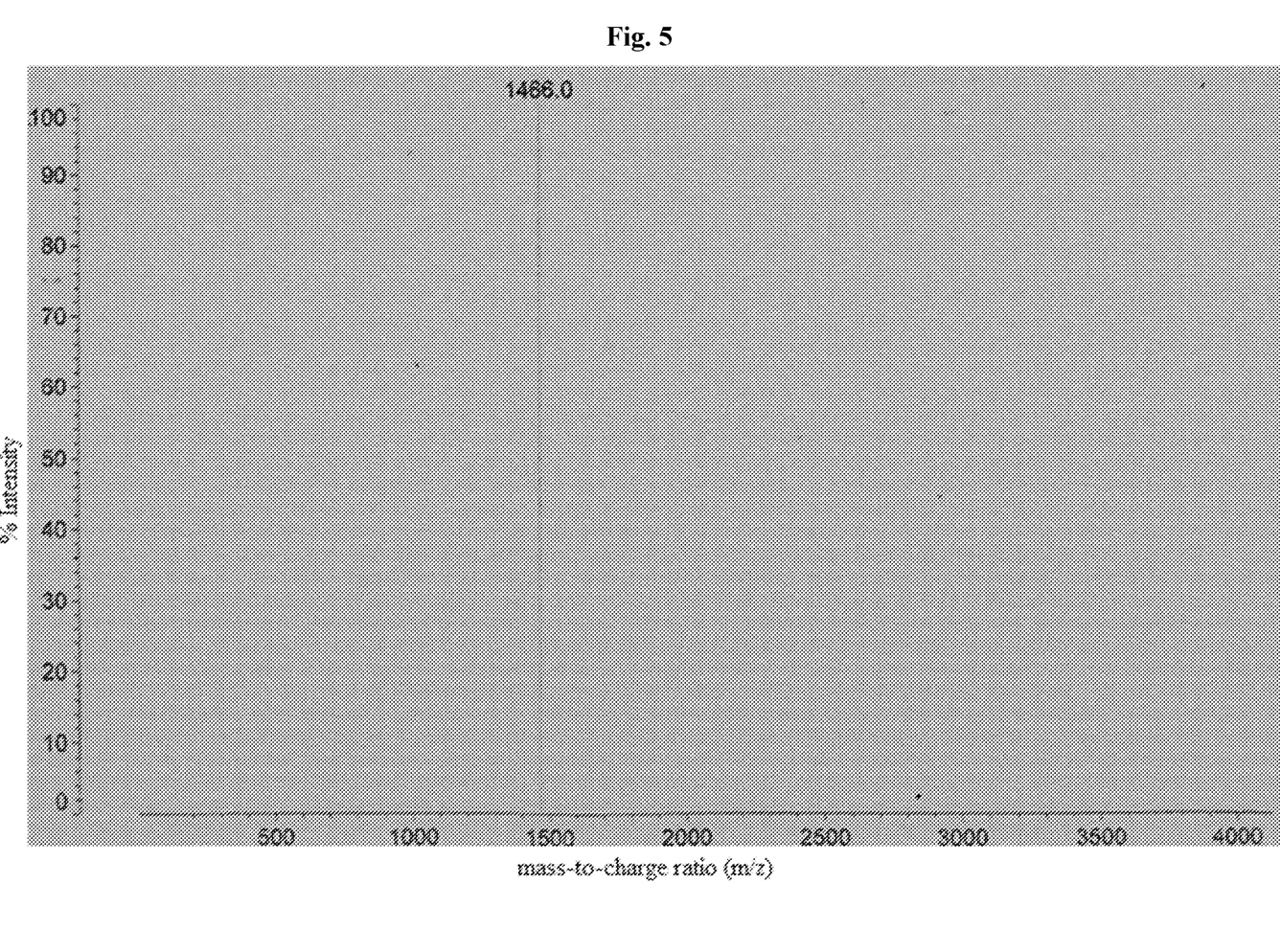
FIG. 5 shows the result of determining the molecular weight of the peptide derived from skate skin.

As a result, it was found that the peptide derived from skate skin is a small-sized peptide of 1,466 Da (FIG. 5). For the amino acid sequence of the peptide derived from skate skin, Edman degradation was used, and the sequence is described as SEQ ID NO: 1.

Example 6. Measurement of Erythrocyte Hemolytic Activity

To determine the cytotoxicity of the peptide, the erythrocyte hemolytic activity was measured as described below.

Specifically, human erythrocytes were washed 3 times with PBS (phosphate-buffered saline, pH 7.0) buffer solution, and then 8.0% erythrocyte solution diluted with PBS buffer was loaded in an amount of 10042 to each wall of a 96-well microtiter plate. Then, the peptide solution of the present invention was mixed therein at a concentration of 1.5, 3.125, 6.25, 12.5, 25, 50, 100, or 200 μM/well, followed by culture for 1 hour at 37° C. After that, the absorbance at a wavelength of 414 nm was measured. As a control group,

The invention claimed is:

1. A method for treating a microorganism infection or inflammation caused by the microorganism, the method comprising administering or applying a composition comprising an antimicrobial peptide with the amino acid sequence of SEQ ID NO: 1 to a subject in need thereof.

2. The method of claim 1, wherein the microorganism comprises at least one of Gram-negative bacteria and Gram-positive bacteria.

3. The method of claim 1, wherein the microorganism comprises Gram-negative bacteria selected from the group consisting of *Escherichia coli, Pseudomonas aeruginosa,* and *Acinetobacter baumannii*.

4. The method of claim 1, wherein the microorganism comprises *Escherichia coli*.

5. The method of claim 1, wherein the microorganism comprises *Pseudomonas aeruginosa*.

6. The method of claim 1, wherein the microorganism comprises *Acinetobacter baumannii*.

7. The method of claim 1, wherein the microorganism comprises *Staphylococcus aureus*.

8. The method of claim 1, wherein the composition is an antibiotic composition comprising the antimicrobial peptide and additional antibiotics other than the antimicrobial peptide.

9. The method of claim 8, wherein the antibiotics comprises at least one selected from the group consisting of aminoglycoside-based antibiotics, penicillin-based antibiotics, sulfonamide-based antibiotics, beta-lactam based antibiotics, chloramphenicol-based antibiotics, erythromycin-based antibiotics, florfenicol-based antibiotics, fosfmycin-based antibiotics, kanamycin-based antibiotics, lincomycin-based antibiotics, meticillin-based antibiotics, quinolone-based antibiotics, streptomycin-based antibiotics, tetracycline-based antibiotics, trimethoprim-based antibiotics, and vancomycin-based antibiotics.

10. The method of claim 1, wherein the composition is a quasi-drug composition comprising the antimicrobial peptide and a quasi-drug component.

11. The method of claim 10, wherein quasi-drug component comprises at least one selected from the group consisting of a sterilizing cleanser, a shower foam, a mouth wash, a water tissue, a liquid soap, a hand wash, a humidifier filler, a mask, an ointment, a patch, and a filter filler.

12. The method of claim 1, wherein the composition is a cosmetic composition comprising the antimicrobial peptide and a cosmetic component.

13. The method of claim 12, wherein the cosmetic component comprises at least one selected from the group consisting of an anti-oxidant, a stabilizing agent, a solubilizing agent, a vitamin, a pigment, a fragrance, and a carrier.

14. The method of claim 12, wherein the antimicrobial peptide is in an amount of 0.1 to 50% by weight based on the total weight of the antibiotic cosmetic composition.

15. The method of claim 12, wherein the cosmetic composition is in a formulation selected from the group consisting of a solution, a suspension, an emulsion, a paste, a gel, a cream, a lotion, a powder, a soap, a surfactant-containing cleanser, an oil, a powder foundation, an emulsion foundation, a wax foundation, and a spray.

16. The method of claim 1, wherein the composition is a food comprising the antimicrobial peptide and a food additive component.

17. The method of claim 1, wherein the composition is an animal feed comprising the antimicrobial peptide and an animal feed component.

18. The method of claim 1, wherein the composition is an antibiotic biopesticides comprising the antimicrobial peptide and a biopesticide component.

19. The method of claim 1, wherein the composition is a preservative composition comprising the antimicrobial peptide and a preservative agent.

* * * * *